United States Patent [19]

Hakata

[11] 4,101,962

[45] Jul. 18, 1978

[54] ELECTRONIC CALCULATOR FOR DETERMINING BIORHYTHM DATA

[75] Inventor: Masayuki Hakata, Ome, Japan

[73] Assignee: Casio Computer Co., Ltd., Tokyo, Japan

[21] Appl. No.: 698,507

[22] Filed: Jun. 22, 1976

[30] Foreign Application Priority Data

Jun. 24, 1975 [JP] Japan .................................. 50-77866

[51] Int. Cl.² ...................... G06F 15/02; G06F 15/42
[52] U.S. Cl. .................................... 364/413; 364/710; 364/715
[58] Field of Search ............................. 835/152, 156; 340/172.5

[56] References Cited

U.S. PATENT DOCUMENTS 3,855,461  12/1974  Stockwell ............................ 235/156
3,863,060  1/1975   Rode et al. .......................... 235/156

OTHER PUBLICATIONS

Brochure, "HP-65 Fully Programmable Pocket Calculator"; Hewlett-Packard, Nov. 1973.
Catalog, "HP-65 User's Library Catalog of Contributed Programs"; Hewlett-Packard, Sep. 1974.
Computer Program for HP-65, "Biorhythms", G. J. Munsey, Sep. 1974.
Computer Program for HP-65, "Biorhythm-Biological Cycles", R. H. Shudde, Sep. 1974.

Primary Examiner—Jerry Smith
Attorney, Agent, or Firm—Flynn & Frishauf

[57] ABSTRACT

An electronic calculator capable of determining biorhythm which comprises means for calculating a number of days of existence from a data of birth and a specified date; means for computing a number of residual days by dividing the calculated number of days of existence by the cyclic periods or 23 days, 28 days and 33 days of three factors of biorhythm, that is, the physique, sensivitity and intellect respectively; and means for indicating said residual days as biorhythmic indices on a specified date.

20 Claims, 15 Drawing Figures

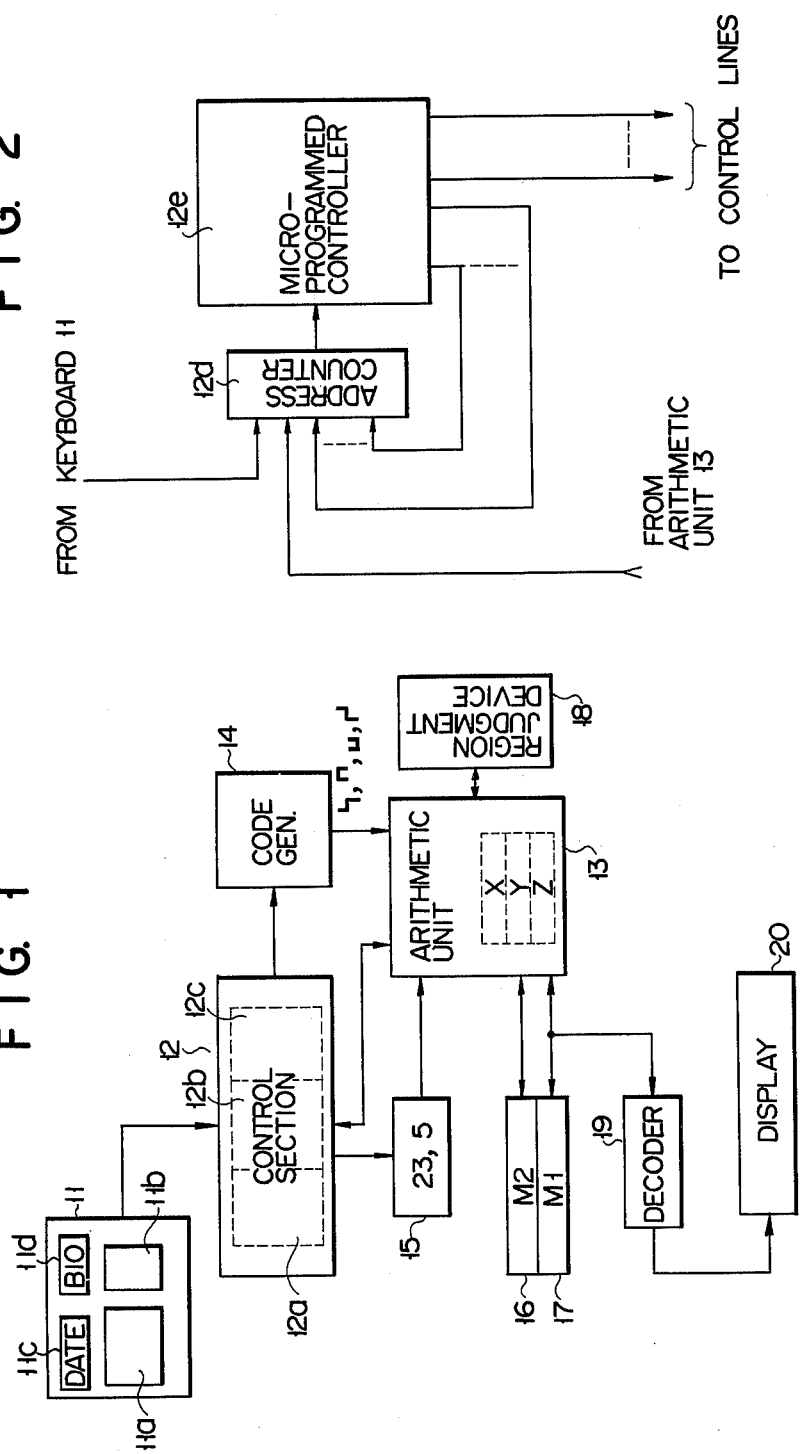

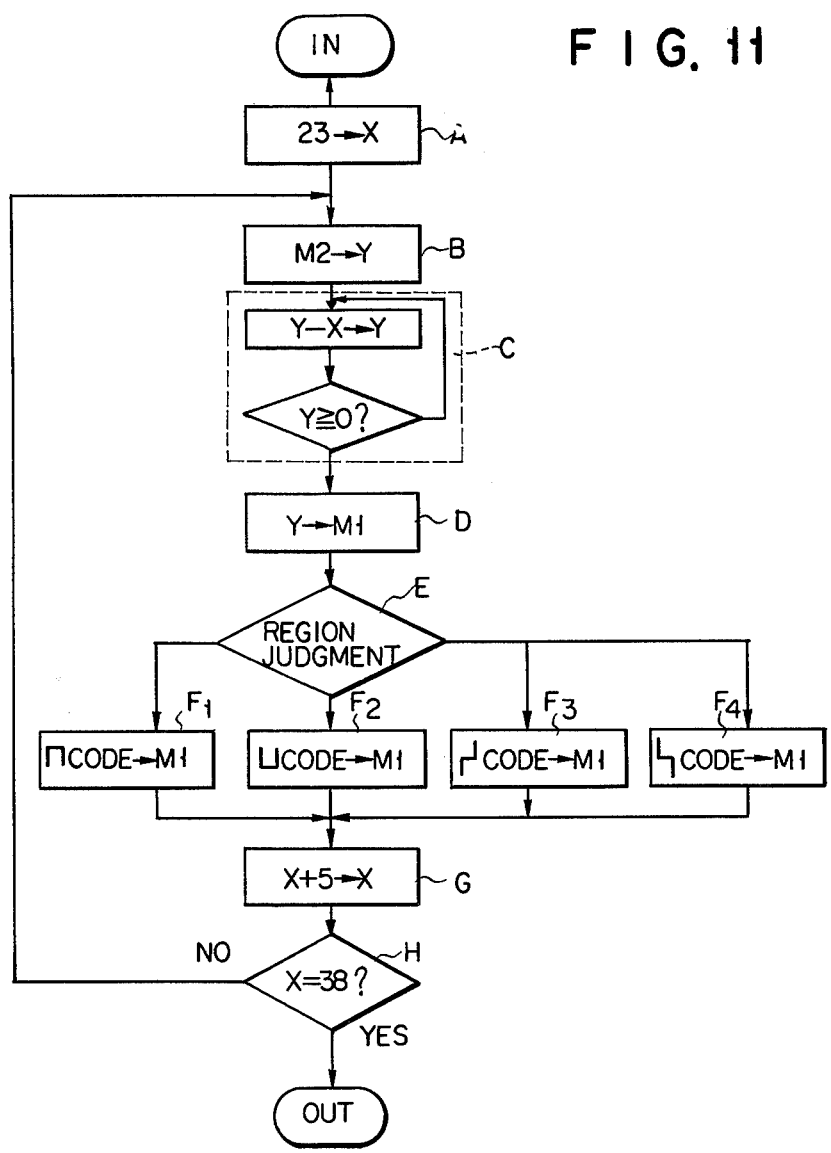

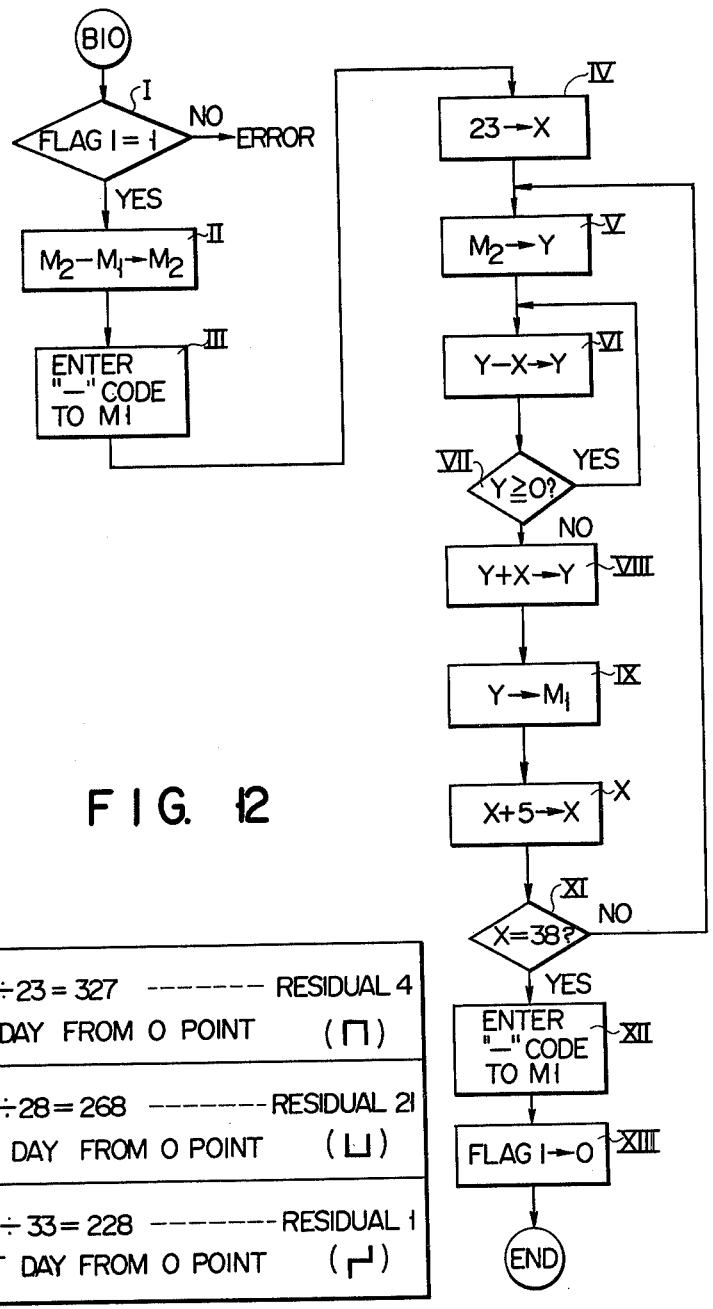

ELECTRONIC CALCULATOR FOR DETERMINING BIORHYTHM DATA

This invention relates to an electronic calculator capable of determining biorhythm.

In recent years, a biorhythmic method of predicting the physical and mental conditions of human beings has come to be widely accepted. Hitherto, however, determination of the biorhythm of human beings has required a biorythm scale device involving complicated calculations and operations. Therefore, the household has been unable easily to find the biorhythm of any family member, giving rise to a strong demand for an apparatus having very compact construction which can be carried anywhere and capable of determining biorhythm on a given date by a simple easy operation.

It is accordingly the object of this invention to provide an inexpensive electronic calculator of simple construction which can quickly determine biorhythm on a desired date at any place by an easy operation.

SUMMARY OF THE INVENTION

According to the present invention, an electronic calculator for determining biorhythm data, comprises an input section having a plurality of number keys for supplying data necessary to effect calculations based on the four fundamental rules of arithmetic and calendar data on the year, month and day; and function keys for instructing various arithmetic operations, including a specific key for instructing the determination of biorhythm. The calculator further includes cardinal number signal generating means for obtaining numerical data representing 23, 28 and 33 days respectively defining the cyclic periods of biorhythm; a control section storing a series of microprograms based on which biorhythm data are to be obtained upon operation of the specific key and displayed, and microprograms based on which the arithmetic operations are to be controlled; an arithmetic operation section controlled by a microprogram read out from the control section upon operation of the specific key, for obtaining a number of days of existence based on the calendar data on birthday and a specific date the biorhythm on which is to be determined, and for dividing said days of existence by the prescribed 23, 28 and 33 days so as to determine a number of residual days (including zero) which serves as biorhythm data, said calendar data having been supplied by operation of the number keys; a memory for storing the three facts of biorhythm, i.e., physique, sensitivity and intellect, in the form of numerical data showing the specific day in each cyclic period on which the three factors of biorhythm are applied; and a display section for displaying the three factors of biorhythm side by side in a predetermined form.

BRIEF DESCRIPTION OF THE DRAWINGS

FIG. 1 is a block circuit diagram of an electronic calculator according to a first embodiment of this invention;

FIG. 2 is a block circuit diagram of a control section of the electronic calculator of FIG. 1;

FIG. 5 gives residual days appearing in the different regions of the cyclic periods of the physique (P), sensitivity (S) and intellect (I) respectively;

FIG. 9 is a flow chart for shifting a number of days obtained from the flow chart of FIG. 8 from an M1 register to an M2 register by continuously operating "−" key used for the four fundamental rules of arithmetic;

FIG. 10 is a flow chart for calculating a number of days between two days by operating "=" key after the data of the two days are entered by using the "−" key;

FIG. 11 is a flow chart for calculating the number of days between the birth date and the specified date and the starting point of reckoning and for determining biorhythm from the number of days thus obtained from the flow charts of FIGS. 8 and 9 by depressing "BIO" key for instructing biorhythm determination;

FIG. 12 gives examples of residual days corresponding to region notations;

FIG. 13 is a flow chart denoting the operation of an electronic calculator according to a second embodiment of this invention;

FIG. 14 is another display pattern of biorhythm obtained from the flow chart of FIG. 13.

DETAILED DESCRIPTION

Figure 4:
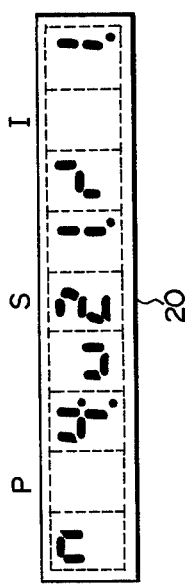
FIG. 4 indicates a practical display pattern appearing on the electronic calculator of FIG. 1.

Referring to FIG. 1, an input section or keyboard 11 of an electronic calculator is provided with ten keys 11a used in presetting digits of 0 to 9; function keys 11b assembled in the calculator and denoting at least notations +, −, ×, ÷, =, etc., used in operations based on the four fundamental rules of arithmetic; day number calculation-instructing key 11c used in supplying data on a birth date and a prescribed date required for determination of biorhythm; and a biorhythm determination-instructing key 11d. An output from the keyboard 11 is conducted to a control section 12. This control section 12 comprises a day number calculation control subsection 12a, biorhythm determination control subsection 12b, and ordinary arithmetic operation control subsection 12c for controlling various forms of operation including at least operations based on the four fundamental rules of arithmetic (hereinafter referred to as "ordinary operations").

The electronic calculator of FIG. 1 executes the operation by using microprogram. Therefore, the control section 12 comprises, as shown in FIG. 2, an address counter 12d and a microprogrammed controller 12e consisting of a read-only memory storing operating steps. When stored with, for example, an ordinal step number of n, then the address counter 12d issues an operation-instructing signal according to said ordinal step number of n. When the operation of the n-th step is brought to an end, then the microprogrammed controller 12e sends forth a signal denoting a step having an immediately higher ordinal number of (n+1)th to the address counter 12d. The later described arithmetic unit 13 supplies the address counter 12d with a signal denoting the conditions like an address jump under which an arithmetic operation is controlled. The microprogrammed controller 12e sends forth an output to control lines. Where the keyboard 11 supplies data on, for example, a birth date and a prescribed date and an instruction of calculating the number of days, then the day number calculation control subsection 12a of the control section 12 is actuated to calculate a number of days of existence. Where the biorhythm determination-instructing key 11d produces a code instructing said determination, the number of days of existence is first obtained by the operation of the subsection 12a and then the biorhythm determination control subsection 12b is put into operation to control biorhythm determination on the basis of a number of days of existence already calculated. The day number calculation control subsection 12a may be of substantially the same arrangement as the day number calculating mechanism set forth in, for example, the U.S. Pat. No. 3,863,060 issued on Jan. 28, 1975. It is advised to construct the biorhythm determination control subsection 12b and ordinary operation control subsection 12c in the same manner as the day number calculation control subsection 12a.

Figure 3:
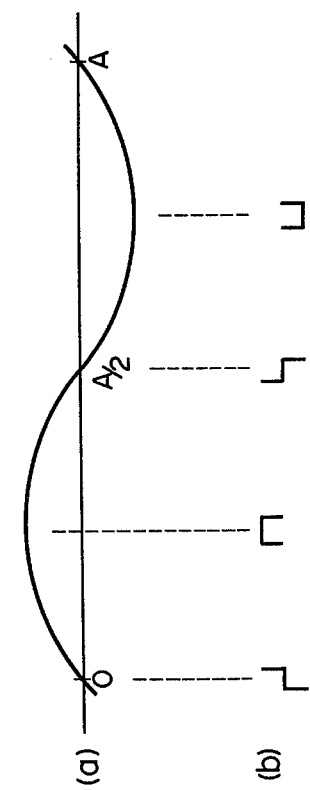
FIG. 3(a) shows a biorhythm curve.
FIG. 3(b) sets forth display notations denoting biorhythmic conditions at different points on the biorhythm curve of FIG. 3(a)

The control section 12 is connected through control lines to the arithmetic unit 13 provided with operation registers X, Y, Z, display code generator 14 and cardinal number generator 15. The arithmetic unit 13 performs various forms of operation by processing data stored in the operation registers X, Y, Z according to an instruction issued by the control section 12. The code generator 14 produces codes denoting four display notations shown in FIG. 3b. Upon receipt of an instruction from the control section, the cardinal number generator 15 issues cardinal numbers of 23 and 5 to indicate the cyclic periods or 23, 28 and 33 days of three factors of biorhythm, that is, the physique (P) sensitivity (S) and intellect (I).

The arithmetic operation section 13 is stored with ordinary data when set for an ordinary operation. When set for biorhythm determination, the arithmetic operation section 13 is connected to first and second registers 17, 16 stored with data on a birth date and a specified date respectively. The first register 17 concurrently acts as a display register stored with that portion of data resulting from various forms of operation which should be displayed. Referential numeral 18 denotes a region judgement device for distinguishing which of the regions included in the cyclic periods of three factors of biorhythm that is, the physique (P), sensitivity (S) and intellect (I) corresponds to each of the numbers of residual days calculated with respect to the three factors of biorhythm. Referential numeral 19 is a decoder for decoding data being displayed. Referential numeral 20 is a display section formed of an electrode shaped like an angular form of a numeral 8 to make a display according to the content of a decoded output from the decoder 19.

There will now be described by reference to FIGS. 3 to 7 the calculation of a number of the above-mentioned residual days and biorhythm determination and the manner in which the results of these operations are displayed. A number of days should be calculated with a leap year and the different numbers of days of the respective months taken into account. Therefore, said calculation is carried out as follows. A date of, for example, March 1 of a zero year of the Christian era is preset as a starting point of reckoning. If $b \geq 3$ is assumed in calculating a number of days up to a date of $c$ days, $b$ months, $a$ years of the Christian era from said starting point of reckoning, then a number of days is calculated by the following formula:

$$[365.25 \times a] + [30.6 \times (b - 3)] + c \tag{1}$$

In case of $b < 3$, the following formula is adopted:
$$[365.25 \times (a - 1)] + [30.6 \times (b + 9)] + c \tag{2}$$

With respect to both formulas, the first term is computed by discarding decimal numbers and the second term is calculated by counting fractions of 0.5 and over as a unit and cutting away the rest. Two forms of day numbers (a number of days from the starting point of reckoning to a birth date and a number of days from the starting point of reckoning to a specified date) are determined by either of the above-mentioned two formulas (1) and (2) of calculation. Subtraction is made between said two forms of day numbers thus calculated followed by proper correction. This operation provides a desired number of days (for convenience of description, hereinafter referred to as "a number of days of existence"). For illustration, a birth date is taken to be Nov. 6, 1954 and a specified date is chosen to be June 13, 1975. Examples of calculations corresponding to this case are given in Table 1 below.

Table 1

| Calculation of days | |
|---|---|
| Days calculated from the starting point of reckoning to a birth date | 713,949 |
| Days calculated from the starting point of reckoning to a specified date | 721,473 |
| Calculated days of existence | 7,524 |
| Days of existence corrected by adding one day | 7,525 |

In this case, both birth date and specified date fall after March 1st of a zero year of the Christian era used as a starting point of reckoning. Therefore, days are calculated by the formula (1), obtaining 713,949 days as a length of time passed from the starting point of reckoning to a birth date and 721,473 days as a length of time passed from the starting point of reckoning to a specified date. Thereafter 713,949 days are subtracted from 721,473 days, followed by correction of adding one day to the balance, thus providing 7,525 days as a number of days of existence.

Where the starting point of reckoning is set as March 1st of an $x$ year (leap year), the formulas (1) and (2) can be rewritten as follows.

$$[365.25 \times (a - x)] + [30.6 \times (b - 3)] + c \tag{3}$$

$$[365.25 \times (a - x - 1)] \times [30.6 \times (b + 9)] + c \tag{4}$$

Figure 6:
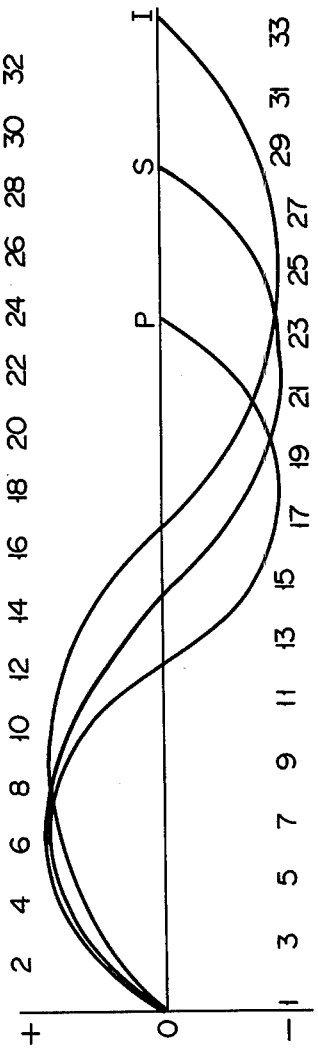
FIG. 6 graphically presents the interrelationships of the physique, sensitivity and intellect.
Figure 7:
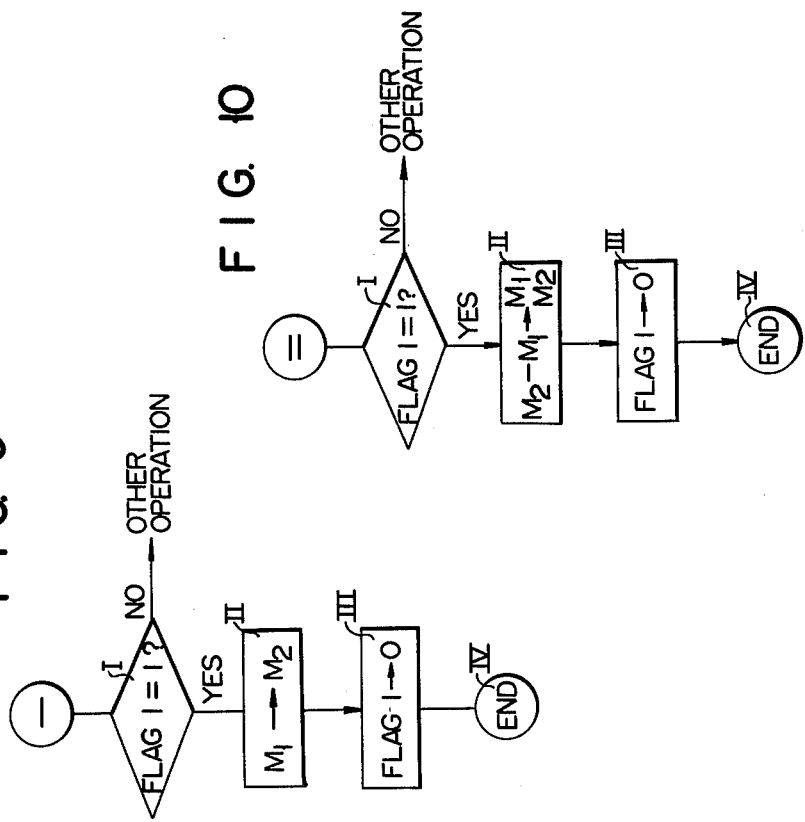
FIG. 7 shows display notations denoting the different regions of said cyclic periods and the corresponding codes.

There will now be described the three cyclic periods of the physique (P), sensitivity (S) and intellect (I) jointly denoting biorythm and the manner in which these three factors of biorythm are displayed. The biorythm consists of the physique (P) having a cyclic period of 23 days, the sensitivity (S) having a cyclic period of 28 days and the intellect (I) having a cyclic period of 33 days. To determine the biorythmic features of (P) the above-mentioned number of days of existence is divided by 23 days denoting the corresponding cyclic period to find a number of residual days. To determine the biorythmic features of (S) and (I), the number of days of existence is divided by 28 days and 33 days representing the corresponding cyclic periods to find numbers of the respective residual days. Thereafter, judgment is made to decide which of the regions included in the respective cyclic periods of (P), (S) and (I) corresponds to each of the respective numbers of residual days. Results of said judgment are displayed in the display panel. FIGS. 3(a), 3(b) and 4 illustrate the manners in which said judgment is made and the corresponding data is displayed. Referring to FIG. 3(a), a curve extending from point 0 to point A represents one of the cyclic periods of (P), (S) and (I). Where residual days have a number falling within the range in which the negative region of the cyclic period is changed to the positive region, then said residual days are displayed in the form of a notation "⌐" shown in FIG. 3(b). Where residual days have a number falling within a stable range included in the positive region of the cyclic period (2 to 11 days in the case of, for example, P as shown in FIG. 5), then the number of said residual days is displayed in the form of a notation "⊓". Where residual days have a number falling within the range in which the positive region of the cyclic period is changed to the negative region of the cyclic period, that is, the range occupying the halfway position of the curve 0A, then the number of said residual days is displayed in the form of a notation "⌐₁". Where residual days have a number falling within a stable range included in the negative region of the cyclic period, then the number of said residual days is displayed in the form of a notation "⊔". These displays can be effected by selectively lighting the corresponding display segments of a display element formed of an electrode shaped like an angular form of a numeral 8. It is possible to present said features by a combination of a number of residual days and the corresponding display notation. Since the crossover point of the biorhythmic curve and the basic line in FIG. 3(a) is important in the biorhythm, it is also possible to present the biorhythmic features of the physique (P), sensitivity (S) and intellect (I) only by the above-mentioned display notations. FIG. 5 shows the numbers of residual days calculated with respect to (P), (S) and (I) and the corresponding display notations. FIG. 6 graphically illustrates the interrelationships of (P), (S) and (I). FIG. 7 indicates the 4-bit code arrangements corresponding to the aforesaid display notations "⊓", "⊔", "⌐" and "⌐₁".

There will now be described the operation of the electronic calculator of this invention which can display the biorhythm of human beings. Where an ordinary arithmetic operation is carried out, data of operation are preset, as in an ordinary electronic calculator, by the ten numerical keys 11a of the keyboard 11 and functional keys 11b for arithmetic operation, and the ordinary arithmetic operation control subsection 12c of the control section 12 is actuated. The arithmetic operation section 13 carries out arithmetic operation under control of an instruction supplied from a microprogram in said control subsection 12c. The data of arithmetic operation is conducted to the display section 20 through the first register 17 and decoder 19.

Figure 8:
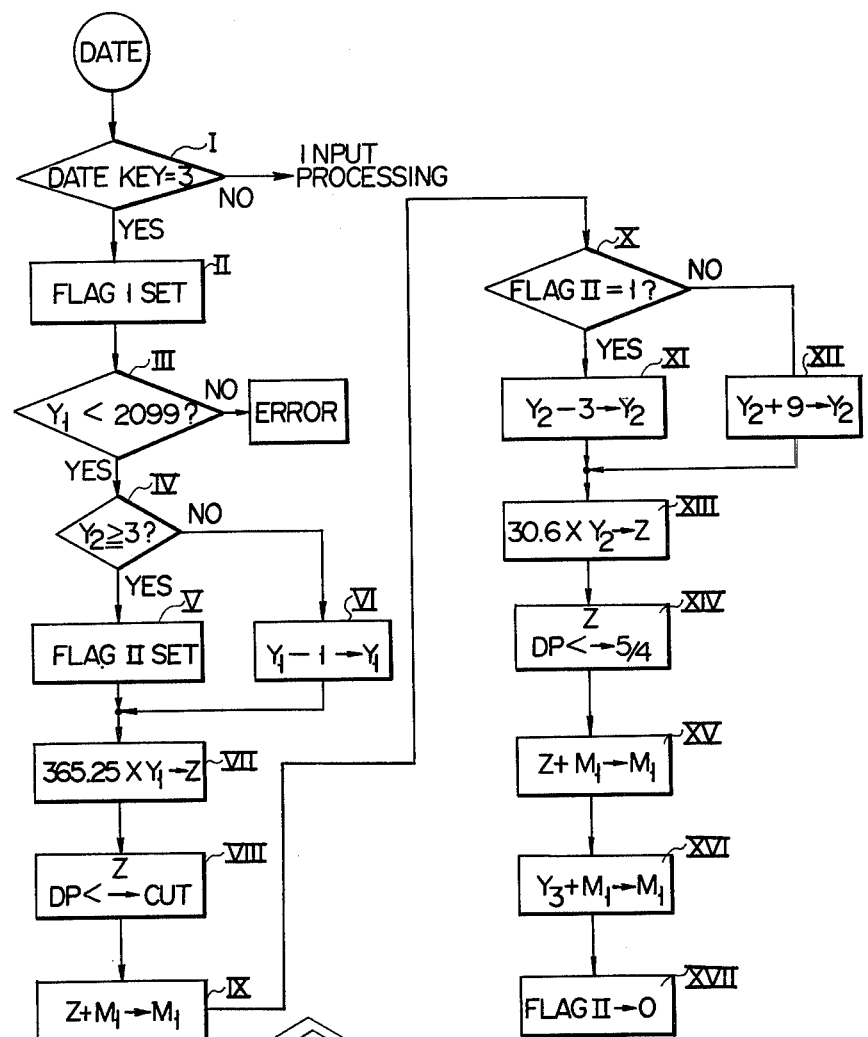
FIG. 8 is a flow chart for calculating a number of days from a starting point of reckoning to the specified date.

Where, for biorhythm determination, a birth date of, for example, June 13, 1975 is preset by the ten keys 11a of the keyboard 11 and day number calculation instructing key 11c, then these keys are operated in the order of "1", "9", "7" "5" "DATE"; "6" "DATE"; and "1", "3", "DATE". For presetting of a date specified for biorhythm determination, the keys are operated likewise. When the "DATE" key 11c is first depressed at the time of entering the data of the birth date, the data is stored in the first step I of the flow chart in FIG. 8. In this first step I, when the number of operations of the "DATE" key 11c is two or less, the data is processed at the input processing section. When the ten keys 11a are operated in the proper order and the "DATE" key 11c is operated three times in presetting a birth date, then all data on said birth date are supplied to the registers Y1, Y2, Y3 in the Y register. Thus the operation step is shifted, as shown in FIG. 8, from the first step I to a second step II. When flag I representing that the all data on the birth date are entered is stored in, for example, Y register in the second step II, the content of the Y1 register is examined in a third step III. If the content is smaller than 2099, then the content is transferred to a fourth step IV. If the content is larger than 2099, then "ERROR" is displayed. The numeral "2099" means the year 2099 of the Christian era selected as a suitable future range for biorhythm determination. Obviously, any other year of the Christian era may be adopted. In the fourth step IV, examination is made to find whether the content of the Y2 register is larger than 3. If the content is larger than 3, then operation proceeds to a fifth step V where Flag II for storing the matter that the content is larger than three is set. The Flag II is stored in the Y register in the similar manner as the Flag I. If the content is smaller than 3, then operation is shifted to a sixth step VI where a numeral 1 is subtracted from the content of the Y1 register. A balance obtained from said subtraction is again preset in the Y1 register. When operation in the fifth step V or sixth step VI is brought to an end, then operation goes on to a seventh step VII, where the content of the Y1 register is multiplied by 365.25. The product is stored in a Z register. Operation is moved on to an eighth step VIII, where decimals included in the content of the Z register are cut away. The content of the Z register thus treated is added to the content of a pre-cleared M1 register in a ninth step IX. The resultant sum is again stored in the M1 resistor. When the ninth step IX is completed, examination is made in a tenth step X to find whether Flag II is set. If Flag II is set, then a balance arrived at by subtracting 3 from the content of the Y2 register is again stored in the Y2 register in an eleventh step XI. If Flag II is not set, then a sum arrived at by adding 9 to the content of the Y2 register is again stored in the Y2 register in a twelfth step XII. Operation of the eleventh XI or twelfth XII step is transferred to a thirteenth step XIII, where the content of the Y2 register is multiplied by 30.6. The product is stored in the Z register. In a fourteenth step XIV, fractions of 0.5 and over included in the decimals of the content of the Z register are counted as a unit and the rest of said decimals is cut away. In a fifteenth step XV, the content of the Z register thus treated is added to the content of the M1 register. The sum is stored in said M1 register. In a sixteenth step XVI, the content of the Y3 register is added to the content of the M1 register. The sum is stored in the M1 register. Thus, a calculation of days based on the aforesaid birth date conducted by the formula (1) or (2) is brought to an end. When a desired number of days is stored in the M1 register, Flag II is reset in a seventeenth step XVII. Operation is shifted to an eighteenth step XVIII.

Thereafter to determine a number of days of existence, subtraction is made through the steps of FIG. 9 between a number of days calculated on the basis of a birth date and a number of days computed on the basis of a specified date. When the minus "−" key included in the function keys 11b is pushed, examination is made in a first step I to find whether Flag I is set. If Flag I is set, then the content of the M1 register is shifted to the M2 register in a second step II. If Flag I is not set, then a day-calculating mode is not established. Therefore, an ordinary arithmetic operation, for example, is carried out. When the second step II is finished, and Flag I is reset in a third step III, then operation proceeds to a final fourth step IV. Since at this time, the M1 register is freed of content, days are calculated on the basis of a specified date as in FIG. 8. When the M1 register is stored with the result of the second calculation of days, subtraction is carried out through the steps of FIG. 10 between both day numbers. When the equal "=" key included in the function keys 11b is pushed, then examination is made in a first step I to find whether Flag I is set. If Flag I is set, then operation is carried out in a second step II to determine a difference between the contents of the M1, M2 registers, thereby providing a number of days of existence. If Flag I is not set, then another form of operation is carried out. When the second step II is brought to an end, the Flag I is reset in a third step III, and operation is finished in a fourth step IV.

Where biorhythm is determined from the above-mentioned two day-calculating operations without displaying a number of days of existence, then said determination is effected in accordance with the flow chart of FIG. 11. The day number calculation control subsection 12a of the control section 12 is actuated. Upon receipt of a control instruction from the control subsection 12a, data on the number of days from the starting point to the specified date is stored in the second register 16 and data on the number of days from the starting point to the birth date is stored in the first register 17. And the biorhythm determination-instructing key 11d is pushed, then the biorhythm determination control subsection 12b of the control section 12 is put into operation. As the result, after the similar operation of the calculation on the days of existence is performed biorhythm is determined from the calculated number of days of existence, using the cardinal number of 23 and 5 obtained from the cardinal number generator 15. There will now be described by reference to FIGS. 11, 12 the operation used in the above-mentioned case. After the calculation on the days of existence is performed, the cardinal numbers issued from the cardinal number generator 15 are preset in an X register of the arithmetic operation section 13, and the number of days of existence is preset in a Y register (steps A, B in FIG. 11). Thereafter subtraction is continued until the content of the Y register has a number equal to or smaller than that of the X register. The resulting residual days are stored in the Y register (step c of FIG. 11). When the number of days of existence is taken to be 7,525 days as shown in Table 1, the residual days relative to the physique (P), sensitivity (S) and intellect (I) are given in FIG. 12. The residual days obtained are read out from the Y register to the first register 17, and then conducted to the region judgment device 18 together with the content of the X register. Judgment is made to decide which of the regions of the physique (P) having a cyclic period of 23 days, the sensitivity (S) having a cyclic period of 28 days and the intellect (I) having a cyclic period of 33 days corresponds to each of the residual days obtained (steps D and E of FIG. 11). Where, as the result of judgmet, a number of residual days calculated with respect to, for example, the intellect (I) is found to be equal to the content of the X register, that is, represent the first day on a curve denoting the cyclic period of the intellect (I) (FIG. 3), then a code denoting a display notation "⌐" which is produced by the code generator 14 is stored in the first register 17. Where the residual days have a number falling within the range in which the positive region of the cyclic period of the intellect (I) is changed to the negative region, namely, corresponding to half the content of the X register, then a code representing a display notation "⌐" which is generated by the code generator 14 is stored in the first register 17. Where the residual days have different numbers, a code showing a display notation "⊓" or "⊔" is stored in the second register 17 according as the number of the residual days exceeds half the content of the X register or falls short of said content. The display notation "⊓" means that the residual days have a number falling within a stable range included in the positive region of the cyclic period. The display notation "⊔" means that the residual days have a number falling within a stable range included in the positive region of the cyclic period. The above-mentioned operations are carried out in the steps F1, F2, F3 and F4 respectively. (Refer to FIGS. 5 and 7).

Later where the content of the X register is changed by adding a cardinal number 5 (step G of FIG. 11) and the increased content of the X register is found to be a smaller number than 38 (that is, 28 or 33), then operation is returned to the step B (step H of FIG. 11). Thereafter, the same operation as mentioned above is repeated. Thus, the biorhythmic periods of the physique (P), sensitivity (S) and intellect (I) are determined in the under mentioned, and stored in the first register 17. Thereafter, all the data is supplied to the display section 20 through the decoder 19. FIG. 4 shows a display pattern of a number of residual days based on, for example, a number of days of existence given in Table 1, proving that biorhythm on a desired date can be shown in an easily visible form.

Figure 15:
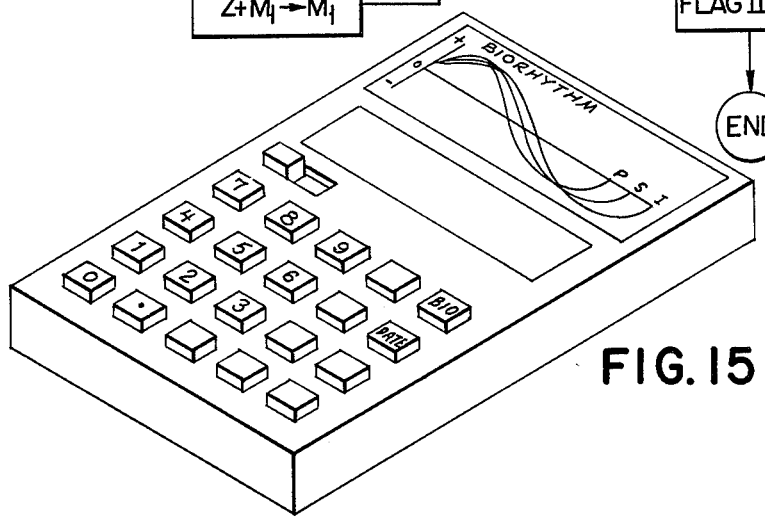
FIG. 15 illustrates a modified calculator of the present invention.

According to the foregoing embodiment, biorhythm was displayed in the form of notations denoting the regions of biorhythm coupled with residual days calculated regarding the three factors (P), (S) and (I) of biorythm. However, as shown in FIG. 15, it is possible to indicate only said residual days on the display panel and attach the graphic representations (shown in, for example, FIG. 6) of the biorhythmic, regions of said three factors to a proper place near the display panel. In such case, it is unnecessary to provide a biorhythmic region judgment device as is utilized in the illustrated embodiment.

Further according to the embodiment, the keyboard 11 was provided with a specific day number calculation-instructing key 11c for presetting a number of days and a specific biorhythm determination-instructing key 11d for determination of biorhythm. However, this invention need not be limited to such arrangement, but may be practised by operating a decimal point key, each time numerals denoting the year, month and day are preset, without providing the day number calculation-instructing key 11c and judging by the control section that when a decimal point code appears at two places of a series of numerals, then said data denotes a calendar date. Further it is possible to determine biorhythm by operating a combination of the selected one of the ten keys 11a and the selected one of the function keys 11b, without providing the specific biorhythm determination instructing key 11d. Further according to the embodiment, biorhythm was displayed in the form of notations "⌐", "⊓", "⌐" and "⊔" denoting the respective biorhythmic regions, using an electrode shaped like an angular form of a numeral 8. However, this invention need not be restricted to such arrangement, but may be practised by displaying biorhythm in the form of numerals or other notations, using another type of display element. For example, it is possible to provide an exclusive display section for biorhythm and indicate the three factors of biorhythm, that is, the physique (P), sensitivity (S) and intellect (I) at the same time, or one after another. Further according to the embodiment, cardinal numbers 23 and 5 required for calculation of the cyclic periods of said three factors (P), (S) and (I) were produced by the cardinal number generator 15. However, this invention may be practised without said generator 15 by presetting the cardinal numbers in a memory and reading them out automatically, where required, in a programming step. It will be noted that this invention can be practised in various modifications without changing the scope and object of the invention.

FIG. 13 is a flow chart of an operation required to display data on the three factors of biorhythm, that is, the physique (P), sensitivity (S) and intellect (I) in a pattern illustrated in FIG. 14. Namely, numerals associated with the (P), (S) and (I) are displayed in series as 23. 21. 06 with a decimal point interposed between the respective factors and said series hyphenated at both ends. In this case, it is advised to recognize the biorhythmic conditions of the (P), (S) and (I) by collating the corresponding residual days with the graphic representations of FIG. 6. With the second embodiment of this invention shown in FIG. 13, a function key "BIO" is pushed instead of the equal key "=" of FIG. 10, when calculations of days based on a birth date and a specified date have been brought to an end. Examination is made in a first step I to find whether Flag I is set. If Flag I is not set, then a signal "ERROR" appears. If Flag I is set, then operation proceeds from the first step I to a second step II, where subtraction is made between the contents of M2 and M1 registers, and a balance is stored in the M2 register. In a third step III, a special code denoting a hyphen is added to the content of the M2 register. When the third step III is finished, a cardinal number 23 is preset in an X register in a fourth step IV. In a fifth step V, the content of the M2 register is preset in a Y register. When the fifth step V is brought to an end, a difference between the contents of the X and Y registers is stored in the Y register in a sixth step VI. Examination is made in a seventh step VII to find whether the content of the Y register is larger than zero. If larger than zero, the content is returned to the sixth step VI. This return operation is continued until the content of the Y register is reduced to zero or has a negative value. Said operation corresponds to an ordinary dividing step to determine a number of residual days associated with the physique (P). If the content of the Y register has a negative value, a sum of the contents of the Y and X registers is determined in an eighth step VIII, and the sum is stored in the Y register. In a ninth step IX, the fresh content of the Y register is shifted to the M1 register. In a tenth step X, a cardinal number 5 is added to the content of the X register, and the sum is stored in said X register. The fresh content of the X register is examined in an eleventh step XI. If the content of the X register is not 38, the content is returned to the fifth step V. Later, a number of residual days relative to the sensitivity (S) having a cyclic period of 23 + 5 = 28 (days) is determined as in the case of (P). If the content of the X register is not 38, then the content is returned to the fifth step V in the eleventh step XI. Thereafter a number of residual days associated with the intellect (I) having a cyclic period of 23 + 5 + 5 = 33 (days) is determined in the same manner as described above. Since, in the eleventh step XI, the content of the X register is now 33 + 5 = 38, a code denoting a hyphen is supplied to the M1 register in a twelfth step XII. When the twelfth step is brought to an end, operation is shifted to a thirteenth step XIII, where Flag I is reset. Thus, operation is brought to a final step END, presenting a biorhythmic pattern of FIG. 14 hyphenated at both ends.

As mentioned above, the electronic calculator of this invention can determine biorhythm by a simple operation at any place and time and display the results of said determination as well as those of ordinary arithmetic operation, admitting of practical application over a broad range.

What is claimed is:

1. Non-programmable electronic calculator for determining biorhythm data, comprising:

an input section comprising a plurality of number keys for supplying data necessary to effect calculations based on the four fundamental rules of arithmetic and calendar data on the year, month and day; and function keys for instructing various arithmetic operations, including a specific key for instructing the determination of biorhythm;

cardinal number signal generating means for obtaining numerical data representing 23, 28 and 33 days respectively defining the cyclic periods of biorhythm;

a control section storing a series of microprograms based on which biorhythm data are to be obtained upon operation of said specific key and displayed, and microprograms based on which the arithmetic operations are to be controlled;

an arithmetic operation section coupled to said control section and to said cardinal number signal generating means and being controlled by a microprogram read out from said control section upon operation of said specific key, for obtaining a number of days of existence based on the calendar data on birthday and a specific date of biorhythm on which is to be determined, and for dividing said days of existence by the prescribed 23, 28 and 33 days so as to determine a number of residual days (including zero) which serves as biorhythm data, said calendar data having been supplied by operation of said number keys;

a memory for storing data items corresponding to the three factors of biorhythm, i.e., physique, sensitivity and intellect, in the form of numerical data showing the specific day in each cyclic period on which the three factors of biorhythm are applied;

code generating means for generating a code inherent to biorhythm, on the basis of a judgment made as to whether three biorhythm data factors stored in said memory exist on two regions, positive and negative, or on two points corresponding to two transition dates, one transition date from the positive region to the negative region and the other transition date from the negative region to the positive region, said code representing other than a numeral; and a display section coupled to said memory for displaying in a predetermined format said three biorhythm data items which are stored in said memory and for also displaying said non-numeral represented by said code generated by said code generating means to indicate that biorhythm data is being displayed.

2. Non-programmable electronic calculator according to claim 1, wherein said cardinal number signal generating means comprises a cardinal number signal generator for generating numerical data representing "23" and "5"; and further comprising means for adding "23" and "5" to provide the prescribed 23, 28 and 33 days respectively representing the cyclic periods of biorhythm.

3. Non-programmable electronic calculator according to claim 1, wherein said cardinal number signal generating means comprises a microprogram stored in said control section, which includes means for producing numerals "23" and "5" in addition to various control instructions; and further comprising means for adding "23" and "5" to provide the prescribed 23, 28 and 33 days respectively representing the cyclic periods of biorhythm.

4. Non-programmable electronic calculator according to claim 1, further comprising means for dividing a number of days of existence by the prescribed 23, 28 and 33 days respectively representing the cyclic periods of biorhythm, thereby determining a number of residual days (including zero), and said code generating means includes a region-judging section for determining whether said number of residual days coresponds to one or the other of two regions (positive and negative regions) or two points (a day when the positive region is changed to the negative region and a day when the negative region is changed to the positive region) for each of said three factors of biorhythm stored in said memory.

5. Non-programmable electronic calculator according to claim 1, further comprising means for dividing a number of days of existence by the prescribed 23, 28 and 33 days respectively representing the cyclic periods of biorhythm, thereby determining a number of residual days (including zero); and said code generating means includes a region-judging section for determining whether said number of residual days corresponds to one or the other of two regions or two points of each of said three factors of biorhythm; and a code generator coupled to said region-judging section for issuing at least four different forms of non-numeric codes as a function of the output from said region-judging section.

6. Non-programmable electronic calculator according to claim 5, further comprising a decoder coupled to said code generator for converting a particular code delivered from said code generator into a data item denoting a prescribed notation, and said display section includes a mosaic display for indicating an output from the decoder.

7. Non-programmable electronic calculator according to claim 6, further comprising display control means for displaying a non-numeric notation represented by a particular code issued from the code generator in juxtaposition with numerical data corresponding to said three factors of biorhythm, i.e., physique, sensitivity and intellect, which are defined by said corresponding residual days.

8. Non-programmable electronic calculator according to claim 7, further comprising display control means for indicating a notation represented by a particular code generated by said code generator in one digit position and data corresponding to each factor of biorhythm in two digit positions.

9. Non-programmable electronic calculator according to claim 1, wherein said display section includes a single multidigit type mosaic display device, and display control means for indicating on said display section data used in calculations based on the four rules of arithmetic, and the results of said calculations in exclusion of calendar data applied to determination of biorhythm and numerical data on the three factors of biorhythm or vice versa.

10. Non-programmable electronic calculator according to claim 9, wherein said display control means includes means for indicating data on the three factors of biorhythm by interposing a period between the adjacent data and by hyphenating the entire biorhythm information at both ends.

11. Non-programmable electronic calculator according to claim 1, further comprising a curve diagram of biorhythm in the prescribed position near said display section, the diagram comprising three curves, each respectively representing one cyclic period of the three factors of biorhythm, i.e., physique, sensitivity and intellect.

12. Non-programmable electronic calculator according to claim 1, wherein said code generating means comprises a region judging section for judging whether each of said biorhythm data factors stored in said memory exist in two regions; and a code generator for generating four kinds of specific codes on the basis of the output of said region judging section, said specific codes representing other than a numeral.

13. Non-programmable electronic calculator for determining biorhythm data, comprising:
an input section comprising a plurality of number keys for supplying data necessary to effect calculations based on the four fundamental rules of arithmetic and calendar data on the year, month and day; and function keys for instructing various arithmetic operations, including a specific key for instructing the determination of biorhythm;
cardinal number signal generating means for obtaining numerical data representing 23, 28 and 33 days respectively defining the cyclic periods of biorhythm;
a control section storing a series of microprograms based on which biorhythm data are to be obtained upon operation of said specific key and displayed, and microprograms based on which the arithmetic operations are to be controlled;
an arithmetic operation section coupled to said control section and to said cardinal number signal generating means and being controlled by a microprogram read out from said control section upon operation of said specific key, for obtaining a number of days of existence based on the calendar data on birthday and a specific date of biorhythm on which is to be determined, and for dividing said days of existence by the prescribed 23, 28 and 33 days so as to determine a number of residual days, including zero, which serves a biorhythm data, said calendar data having been supplied by operation of said number keys;
a memory for storing data items corresponding to the three factors of biorhythm, i.e., physique, sensitivity and intellect, in the form of numerical data corresponding to the specific day in each cyclic period on which the three factors of biorhythm are applied;

specific code generating means coupled to said memory for generating a specific non-numeric code indicating that the data in said memory are biorhythm data and for inputting them in said memory for storage;

display control means for inserting a marker at least between each of the biorhythm data items stored in said memory; and a display section for displaying in a predetermined format said biorhythm data stored in said memory, said specific non-numeric code and said marker generated from said display control means.

14. Non-programmable electronic calculator according to claim 13, wherein said specific code generating means comprises means for generating hyphen codes and control means for inputting the hyphen codes generated by said generating means to add them one at each of the outside ends of said biorhythm data stored in said memory such that the biorhythm data is so displayed by said display section with a hyphen at each outside end thereof.

15. Non-programmable electronic calculator according to claim 13, wherein said specific code generating means comprises means for generating hyphen codes and display control means for inputting the hyphen codes generated by said generating means to add them one at each of the outside ends of said biorhythm data stored in said memory to permit the overall biorhythm data to be so displayed with hyphens at each end thereof, said display control means further comprising means controlled to display a decimal point between each biorhythm data item, said biorhythm data being displayed on said display section with the hyphens added one at each of the outside ends of said overall biorhythm data and with the decimal points added one between each biorhythm data item.

16. Non-programmable electronic calculator according to claim 13, wherein said display section comprises a single multi-digit mosaic type display device on which is provided means for effecting exclusive control display of data used in the arithmetic operation, data resulting therefrom, date data used in biorhythm, and biorhythm data.

17. Non-programmable electronic calculator according to claim 13, wherein said cardinal number signal generating means comprises a cardinal number signal generator for generating numerical data representing "23" and "5"; and further comprising means for adding "23" and "5" to provide the prescribed 23, 28 and 33 days respectively representing the cyclic periods of biorhythm.

18. Non-programmable electronic calculator for determining biorhythm data as claimed in claim 17 wherein said cardinal number signal generating means comprises a microprogram stored in said control section, which includes means for producing numerals "23" and "5" in addition to various control instructions; and further comprising means for adding "23" and "5" to provide the prescribed 23, 28 and 33 days respectively representing the cyclic periods of biorhythm.

19. Non-programmable electronic calculator according to claim 13, further comprising a biorhythm curve chart provided at a predetermined position adjacent to said display section and located so as to be visible to the user concurrently with said display section without requiring moving of said calculator, one cycle of each of biorhythm curves representing three factors of physique, sensitivity and intellect being displayed on said curve chart.

20. Non-programmable electronic calculator for determining biorhythm data, comprising:

an input section comprising a plurality of number keys for supplying data necessary to effect calculations based on the four fundamental rules of arithmetic and calendar data on the year, month and day; and function keys for instructing various arithmetic operations, including a specific key for instructing the determination of biorhythm;

cardinal number signal generating means for obtaining numerical data representing 23, 28 and 33 days respectively defining the cyclic periods of biorhythm;

a control section storing a series of microprograms based on which biorhythm data are to be obtained upon operation of said specific key and displayed, and microprograms based on which the arithmetic operations are to be controlled;

an arithmetic operation section coupled to said control section and to said cardinal number signal generating means and being controlled by a microprogram read out from said control section upon operation of said specific key, for obtaining a number of days of existence based on the calendar data on birthday and a specific date of biorhythm on which is to be determined, and for dividing said days of existence by the prescribed 23, 28 and 33 days so as to determine a number of residual days (including zero) which serves as biorhythm data, said calendar data having been supplied by operation of said number keys;

a memory for storing the three factors of biorhythm, i.e., physique, sensitivity and intellect, in the form of numerical data showing the specific day in each cyclic period on which the three factors of biorhythm are applied;

a display section coupled to said memory for displaying said three factors of biorhythm side by side in a predetermined format; and a biorhythm curve chart provided at a predetermined position adjacent to said display section and located so as to be visible to the user concurrently with said display section without requiring moving of said calculator, one cycle of each of biorhythm curves representing three factors of physique, sensitivity and intellect being displayed on said curve chart.

* * * * *